(12) United States Patent
Guo et al.

(10) Patent No.: US 12,139,582 B2
(45) Date of Patent: Nov. 12, 2024

(54) MODIFIED ALLYL COMPOUND, MODIFIED BISMALEIMIDE PREPOLYMER

(71) Applicant: GUANGDONG HINNO-TECH CO., LTD., Jiangmen (CN)

(72) Inventors: Yongjun Guo, Jiangmen (CN); Wenyan Wen, Jiangmen (CN); Xinquan Zhang, Jiangmen (CN); Rongqiang Liang, Jiangmen (CN)

(73) Assignee: GUANGDONG HINNO-TECH CO., LTD., Jiangmen (CN)

( * ) Notice: Subject to any disclaimer, the term of this patent is extended or adjusted under 35 U.S.C. 154(b) by 536 days.

(21) Appl. No.: 17/541,722

(22) Filed: Dec. 3, 2021

(65) Prior Publication Data

US 2022/0204699 A1    Jun. 30, 2022

(30) Foreign Application Priority Data

Dec. 22, 2020  (CN) .......................... 202011524360.3

(51) Int. Cl.
*C08G 73/12*    (2006.01)
(52) U.S. Cl.
CPC ........... *C08G 73/128* (2013.01); *C08G 73/12* (2013.01); *C08G 73/127* (2013.01)
(58) Field of Classification Search
CPC ..... C08G 73/12; C08G 73/128; C08G 73/127
See application file for complete search history.

(56) References Cited

FOREIGN PATENT DOCUMENTS

| CN | 103131008 A |   | 6/2013 |            |
|----|-------------|---|--------|------------|
| CN | 106977717 A | * | 7/2017 | C08G 73/123 |
| CN | 107459650 A |   | 12/2017 |           |
| JP | 2011127063 A |  | 6/2011 |            |
| JP | 2013166929 A |  | 8/2013 |            |
| JP | 2019210451 A |  | 12/2019 |           |

OTHER PUBLICATIONS

Qu et al Novel allyl and propenyl monomers for modification of the bismaleimide resins, with excellent dielectric properties and high glass transition temperatures, High Performance Polymers 2020, vol. 32(1) 116-126, published on Jan. 2020.*
Japanese Office Action, and English translation thereof, for counterpart Japanese Application No. 2021-204018, mailed Dec. 6, 2022 (6 pages).
Hua Yong, "Research on Modified BMI Resin," Journal of Zhengzhou Polytechnic Institute, vol. 17, No. 4, Dec. 2001, (2 pages). (English Abstract only; See CN Office Action for Chinese Counterpart Application No. 202011524360.3, mailed Aug. 3, 2022, and cited in IDS on Sep. 23, 2022).
First Chinese Office Action, and English translation thereof, for Chinese Counterpart Application No. 202011524360.3, mailed Aug. 3, 2022, (9 pages).

* cited by examiner

*Primary Examiner* — Gregory Listvoyb
(74) *Attorney, Agent, or Firm* — Kagan Binder, PLLC

(57) ABSTRACT

The present disclosure provides a modified allyl compound, and a modified bismaleimide prepolymer. The modified allyl compound is represented by formula (1), has a cyclopentadiene structure represented by formula (2), and contains a benzene ring or a benzene ring substituted with a linear alkane of lower polarity.

10 Claims, No Drawings

MODIFIED ALLYL COMPOUND, MODIFIED BISMALEIMIDE PREPOLYMER

CROSS REFERENCES TO RELATED APPLICATIONS

This disclosure claims priority to China Patent Application No. 202011524360.3, filed on Dec. 22, 2020, and entitled "modified allyl compound, modified bismaleimide prepolymer, and use thereof", the content of which is hereby incorporated by reference in its entirety.

TECHNICAL FIELD

The present disclosure relates to the technical field of resin preparation, in particular to a modified allyl compound, and a modified bismaleimide prepolymer.

BACKGROUND

With the rapid development of the electronics industry, electronic products are developing in the direction of miniaturization, high functionality, and high security, which require electronic components to have higher signal propagation speed and transmission efficiency. Therefore, higher requirements are put forward on the substrate of the electric board. In addition to requiring high heat resistance, stripping resistance and excellent mechanical properties, the electric board is also required to have lower water absorption, dielectric constant and dielectric loss value.

Conventionally, diamine-modified or allyl-modified bismaleimide resin is often used to prepare electrical board substrates, but with defects such as high curing temperature, high water absorption, high dielectric constant and high dielectric loss value. Those skilled tried to complex other functional resins such as epoxy resins and modified bismaleimide prepolymers to prepare prepregs and copper-clad laminated boards. However, modifiers such as 2, 2'-diallyl bisphenol A (DABPA) are often used in conventional technology for preparation of modified bismaleimide prepolymers. The modifiers can improve the solubility and compatibility of bismaleimide prepolymers, however, would increase the dielectric constant and dielectric loss of the cured product, resulting in the cured product with poor heat resistance and high water absorption, which is difficult to be applied in high-end integrated circuits.

Therefore, it is always a challenge for those skilled in the art to obtain a resin with excellent heat resistance, low water absorption, low dielectric constant and low dielectric loss value.

SUMMARY

Accordingly, the present disclosure provides a modified allyl compound and a modified bismaleimide prepolymer that can reduce the water absorption, dielectric constant, and dielectric loss value of a resin while improving the heat resistance of the resin.

The technical solution of the present disclosure is as follows.

In one aspect, the present disclosure provides a modified allyl compound represented by formula (1):

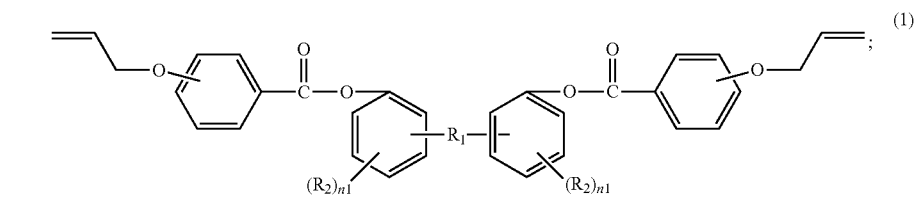

wherein $R_1$ is represented by formula (2):

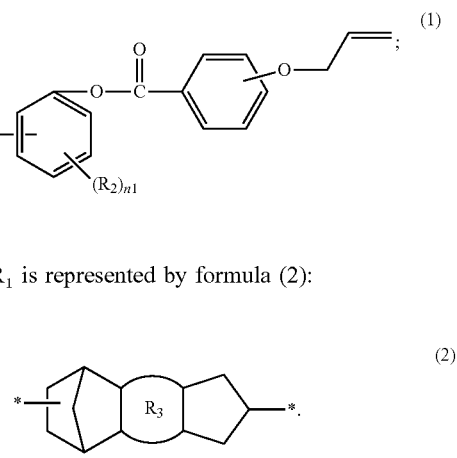

$R_3$ is absent, or is selected from a bicycloheptyl group and a group obtained by condensation of two or more bicycloheptyl groups; * indicates an attachment site:

$R_2$ at each occurrence is independently selected from H and a linear alkyl group having 1 to 10 carbon atoms; $n1$ at each occurrence is independently selected from any integer from 1 to 4.

In some of the embodiments. $R_1$ is selected from any one of formula (2-a) and formula (2-b):

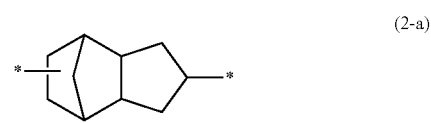

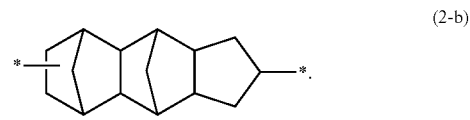

In some of the embodiments, the modified allyl compound is represented by formula (1-1):

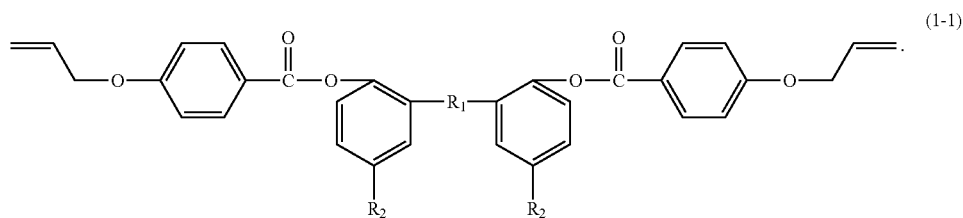

In some of these embodiments, $R_2$ at each occurrence is H.

In some of the embodiments, the modified allyl compound is represented by formula (1-3):

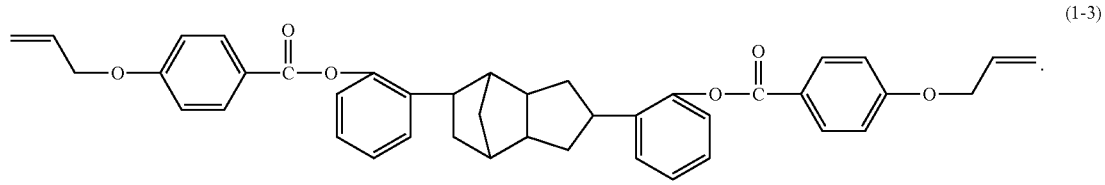 [SMILES: C=CCOc1ccc(C(=O)Oc2ccccc2C2CC3C4CC(c5ccccc5OC(=O)c5ccc(OCC=C)cc5)C(C4)C3C2)cc1]

In some of the embodiments, the modified allyl compound is represented by formula (1-4):

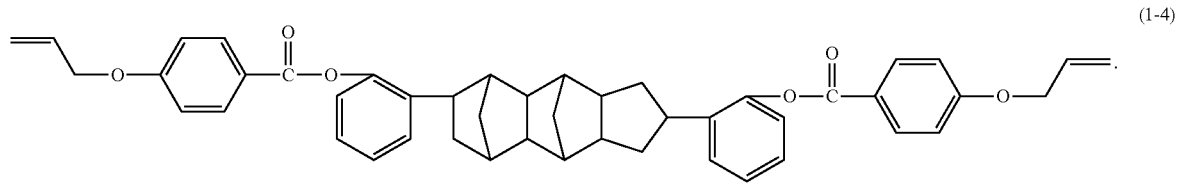 [SMILES: C=CCOc1ccc(C(=O)Oc2ccccc2C2CC3C(C2)C2CC3C3C4CC(c5ccccc5OC(=O)c5ccc(OCC=C)cc5)C(C4)C23)cc1]

In another aspect, the present disclosure provides a modified bismaleimide prepolymer, wherein raw materials for preparing the modified bismaleimide prepolymer comprise bismaleimide resin and the modified allyl compound as described above.

In some of the embodiments, the raw materials comprise by mass:

| | |
|---|---|
| the bismaleimide resin | 100 parts; and |
| the modified allyl compound | 40 parts to 100 parts. |

In some of the embodiments, the raw materials further comprise other allyl compound being at least one selected from the group consisting of diallyl bisphenol A, diallyl bisphenol S, diallyl bisphenol F and bisphenol A diallyl ether; a mass ratio of the other allyl compound and the modified propyl compound is (5 to 40): (40 to 80).

The present disclosure also provides a modified resin composition consisting of a curing accelerator, an inorganic filler, and the modified bismaleimide prepolymer as described above.

The modified allyl compound provided in the present disclosure is represented by formula (1), has a cyclopentadiene structure represented by formula (2), and contains a benzene ring or a benzene ring substituted with a linear alkane of lower polarity. After modifying bismaleimide using the modified allyl compound, the modified bismaleimide prepolymer prepared would have a specific structure and lower polarity, resulting in improved solubility of bismaleimide, thereby reducing the water absorption, dielectric constant and dielectric loss value of the resin, while improving the heat resistance of the resin.

The present disclosure also provides a modified bismaleimide prepolymer. The raw materials for preparing the modified bismaleimide prepolymer comprise bismaleimide resin and the modified allyl compound as described above. The modified bismaleimide prepolymer has a specific structure, resulting in improved solubility and reduced crosslinking density of bismaleimide, thereby reducing the water absorption, dielectric constant and dielectric loss value of the resin, while improving the heat resistance of the resin.

DETAILED DESCRIPTION OF THE EMBODIMENTS

To make the present disclosure easy to understand, a more comprehensive description of the present disclosure will be given below with reference to the embodiments, and better embodiments of the present disclosure are given below. However, the present disclosure can be implemented in many different forms and shall not limited to the embodiments described herein. On the contrary, the purpose of providing these embodiments is to provide a more thorough and comprehensive understanding of the disclosure of the present disclosure.

Unless otherwise defined, all technical and scientific terms used herein have the same meanings as those generally understood by those skilled in the art of the present disclosure. The terms used in the specification of the present disclosure are only intended to describe the purposes of specific embodiments, rather than limiting the present disclosure. The term "and/or" as used herein comprises any and all combinations of one or more related listed items.

In the present disclosure, the same substituent, if occurring multiple times, can be independently selected from different groups. For example, if formula (1) contains multiple $R_2$, $R_2$ can be independently selected from different groups.

In the present disclosure, "*" indicates an attachment site.

In the present disclosure, if there is no specified attachment site in the group, it means that any attachable site in the group can be regarded as the attachment site.

In the present disclosure, a single bond via which a substituent is attached running through the corresponding ring, means that the substituent can be attached to any position of the ring. For example, in

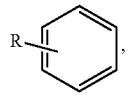

R can be attached to any substitutable site of the benzene ring.

In the conventional laminated board preparation, the skilled person tried to use other functional resins such as epoxy resins and modified bismaleimide prepolymers to prepare prepregs and copper-clad laminated boards. Although the laminated board has better dielectric properties, higher glass transition temperature and good impact toughness, the obtained laminated board has poor heat resistance, high water absorption and high dielectric loss, which makes it difficult to be applied in high-end integrated circuits.

Nevertheless, those skilled have been making an effort to improve the structure of allyl compounds to modify bismaleimide, thereby optimizing the performance of the laminated board. However, due to the complex synergy between the materials of the resin composition, it is always a challenge for those skilled in the art to obtain a resin with excellent heat resistance, low water absorption, high modulus, low dielectric constant and low dielectric loss value.

For example, according to a conventional technical solution, the bismaleimide prepolymer is modified by an allyl compound containing a dicyclopentadiene structure and a strongly polar benzene ring to improve the water absorption and dielectric properties of the laminated board. However, the heat resistance and dielectric properties of the produced laminated board are still difficult to meet the requirements of high-end integrated circuits.

The inventors of this application, based on their years of research experience in the field of printed circuit boards, have discovered through creative experiments that improved solubility and reduced crosslinking density of bismaleimide can be achieved after modifying bismaleimide with an allyl compound containing a dicyclopentadiene structure and a benzene ring or a benzene ring substituted by a linear alkane with lower polarity, and have performed further investigation through a large number of experiments, thereby obtaining the technical solution of the present disclosure.

An embodiment of the present disclosure provides a modified allyl compound represented by formula (1):

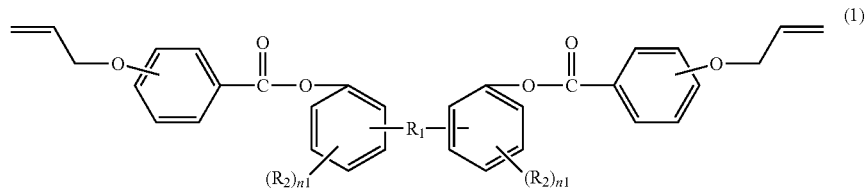

wherein $R_1$ is represented by formula (2):

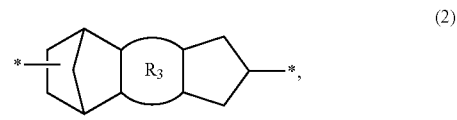

$R_3$ is absent, or is selected from a bicycloheptyl group and a group obtained by condensation of two or more bicycloheptyl groups; * indicates an attachment site;

$R_2$ at each occurrence is independently selected from H and a linear alkyl group having 1 to 10 carbon atoms; $n1$ at each occurrence is independently selected from any integer from 1 to 4.

It can be understood that the bicycloheptyl group is condensed with a cyclopentyl group when $R_3$ is absent in formula (2), which is represented by:

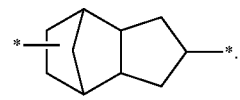

In addition, $R_1$ and $R_2$ would not be attached to the same carbon atom on the same benzene ring in the compound represented by formula (1), since each of the unsubstituted carbon atoms on the benzene ring has only one hydrogen atom.

The above modified allyl compound has a cyclopentadiene-like structure represented by formula (2), and contains a benzene ring or a benzene ring substituted with a linear alkane of lower polarity. When the modified allyl compound is used to modify bismaleimide, the prepared modified bismaleimide prepolymer will have a specific structure, which can improved the solubility of bismaleimide, reduce the cross-linking density, thereby reducing the water absorption, dielectric constant, and dielectric loss value of the resin, while improving the heat resistance of the resin.

In some of the embodiments, $R_1$ is selected from any one of formula (2-a) and formula (2-b):

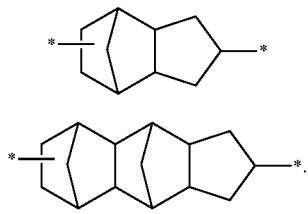

In some of the embodiments, $R_1$ is selected from any one of formula (2-c) and formula (2-d):

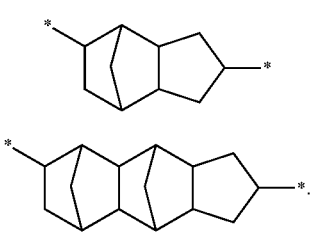

Further, the method for preparing the modified allyl compound is provided, which includes following steps S10 to S30.

Step S10: compound 1 and compound 2 are subjected to grafting reaction under a first catalyst to obtain a first intermediate.

In some of the embodiments, the above-mentioned first catalyst is one or more selected from the group consisting of boron trifluoride ether, boron trichloride ether, boron trifluoride dimethyl ether, and boron trifluoride ethylene diamine.

In some of the embodiments, in step S10, a molar ratio of compounds 1 and 2 is (1-2):1.

In some of the embodiments, compound 1 is any one selected from the group consisting of phenol, and phenol substituted with a linear alkyl group of 1 to 7 carbon atoms.

In some of the embodiments, compound 2 is selected from the group consisting of dicyclopentadiene and tricyclopentadiene.

In some of the embodiments, step S10 specifically includes steps S11 and S12.

Step S11: compound 1 is mixed with the first catalyst, and heated to 80° C. to 150° C., and then compound 2 is added dropwise for 3 h to 10 h, with heating preserved for the reaction for 1 h to 5 h.

Step S12: the reactant after the reaction in step S11 is distilled under reduced pressure to remove unreacted compounds 1 and 2, and then washed with water, added with an organic solvent, and finally filtered and distilled.

In some of the embodiments, the organic solvent as described above is one or more selected from the group consisting of methyl ethyl ketone, cyclohexanone, acetone, diethyl ether, toluene, xylene propylene glycol methyl ether, DMF and NMP.

Step S20: compound 3 and an acylating chlorination reagent are subjected to an acylating chlorination reaction to obtain a second intermediate.

In some of the embodiments, a molar ratio of compound 3 and the acylating chlorination reagent is 1:(1 to 2).

In some of the embodiments, the above-mentioned acylating chlorination reaction is carried out in toluene; further, the above-mentioned acylating chlorination reaction is carried out at 50° C. to 70° C. for 4 h to 8 h.

In some of the embodiments, the above-mentioned acylating chlorination reagent is selected from thionyl chloride.

In some of these embodiments, the compound 3 is 4-allyloxybenzoic acid.

It should be noted that step S10 and step S20 have no specific sequence, and can be performed sequentially or simultaneously.

Step S30: the first intermediate obtained in step 10 and the second intermediate obtained in step 20 are subjected to a substitution reaction under a second catalyst to obtain the modified allyl compound as described above.

In some of the embodiments, the above-mentioned second catalyst is one or more selected from the group consisting of triethylamine, diethylamine, triethanolamine, and triethyl phosphate.

In some of the embodiments, in step S30, a molar ratio of the first intermediate and the second intermediate is 1:(1 to 2).

In some of the embodiments, the substitution reaction in step S30 is carried out in tetrahydrofuran. Further, the substitution reaction is carried out at 50° C. to 70° C. for 10 h to 30 h.

Specifically, in step S30, the second intermediate and the second catalyst are respectively diluted with an organic solvent, and then the second catalyst is added to the diluent of the first intermediate, then the diluent of the second intermediate is added dropwise, and the reaction is carried out at 50° C. to 70° C. for 10 h to 30 h.

Specifically, the above-mentioned organic solvent is tetrahydrofuran.

In some of the embodiments, step S30 further includes a step of recrystallizing the crude product of the substitution reaction; a specific recrystallizing solution is tetrahydrofuran.

Compounds 1 to 3, the first intermediate, and the second intermediate are represented by formulas (a) to (e), respectively:

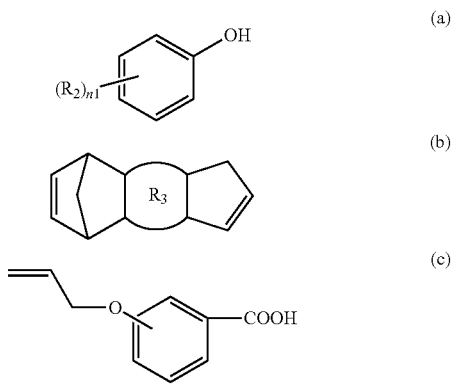

-continued (d)
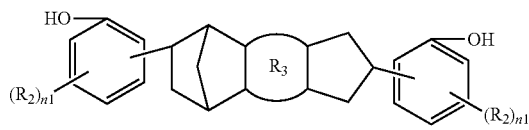

(e)
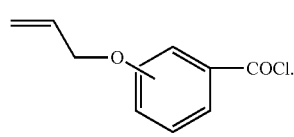

In some of the embodiments, the above-mentioned modified allyl compound is represented by formula (1-1):

(1-1)
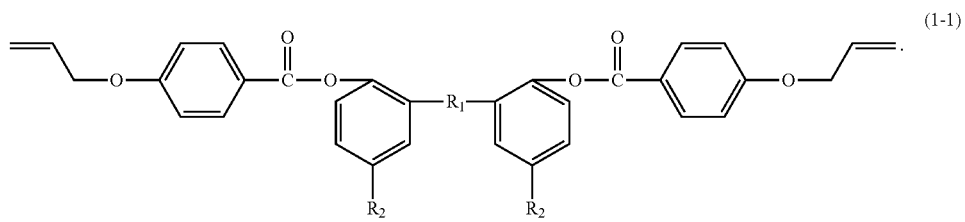

In some of the embodiments, $R_2$ at each occurrence is independently selected from H and a linear alkyl group having 1-7 carbon atoms.

In some of these embodiments, $R_2$ at each occurrence is H.

In some of these embodiments, n1 at each occurrence is independently selected from any integer from 1 to 4. Furthermore, n1 is 4.

In some of the embodiments, the above-mentioned modified allyl compound is represented by formula (1-2):

(1-2)
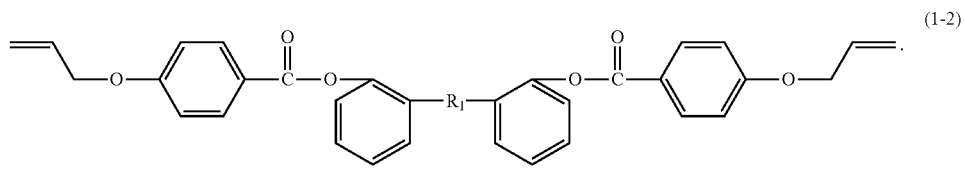

In some of these embodiments, $R_3$ is absent, or is a bicycloheptyl group. Further, the bicycloheptanyl group is a bicyclo[2,2,1]heptanyl group.

Specifically, the above-mentioned modified allyl compound is any one of formulas (1-3) to (1-5):

(1-3)
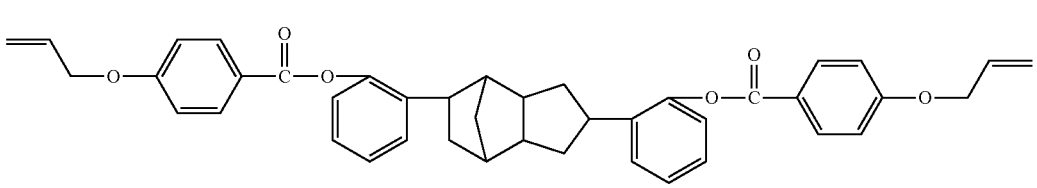

(1-4)
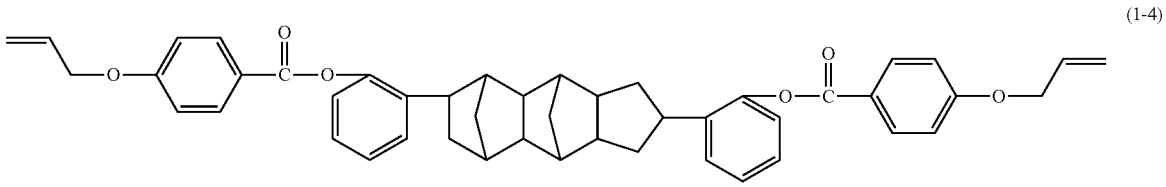

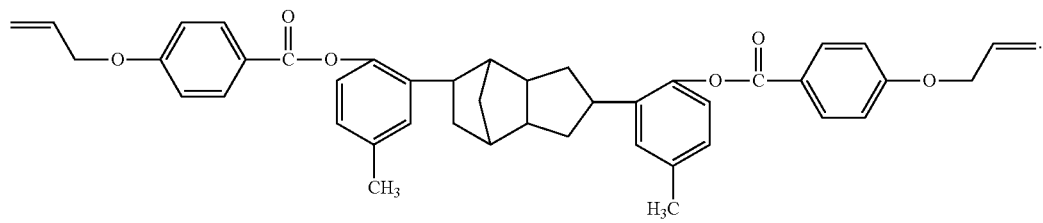

(1-5)

An embodiment of the present disclosure also provides a modified bismaleimide prepolymer, wherein raw materials for preparing the modified bismaleimide prepolymer includes bismaleimide resin and the modified allyl compound as described above.

The modified bismaleimide prepolymer has a specific structure, which can improve solubility and reduce cross-linking density of bismaleimide, thereby reducing the water absorption, dielectric constant and dielectric loss value of the resin, while improving the heat resistance of the resin.

In some of the embodiments, the raw materials includes by mass 100 parts of the bismaleimide resin and 40 parts to 100 parts of the modified allyl compound.

In some of the embodiments, the raw materials includes other allyl compound, which is at least one selected from the group consisting of diallyl bisphenol A, diallyl bisphenol S, diallyl bisphenol F and bisphenol A diallyl ether. A mass ratio of the other allyl compound and the modified propyl compound is (5 to 40): (40 to 80).

It can be understood that the compound represented by formula (1) can be used alone as the modified allyl compound, or in combination with at least one of diallyl bisphenol A, diallyl bisphenol S, diallyl bisphenol F, and bisphenol A diallyl ether.

There is no particular limitation on the bismaleimide resin used to prepare the modified bismaleimide prepolymer of the present disclosure, which can be selected from organic compounds containing two or more maleimide structure's in the molecular structure. The maleimide structure can be at least one of Ni-phenylmaleimide group, N-(2-methylphenyl)maleimide group, N-(4-methylphenyl)maleimide group, N-(2,6-dimethylphenyl)maleimide group, bis(4-maleimidophenyl)methane group, 2,2-bis(4-(4-maleimidophenoxy)-phenyl)propanyl, bis(3,5-dimethyl-4-maleimidophenyl) methane base, bis(3-ethyl-5-methyl-4-maleimidophenyl) methane group, bis(3,5-diethyl-4-maleimidophenyl) methane group, polyphenylmethane bismaleimide group and biphenyl structure-containing maleimide group.

Further, the preparation method of the modified bismaleimide prepolymer as described above includes following step.

The modified allyl compound is heated to a molten state, the bismaleimide resin is added, and prepolymerization is carried out at 120° C. to 180° C., thus obtaining a modified bismaleimide prepolymer.

Further, the time of the above-mentioned prepolymerization is 30 min to 120 min.

It can be understood that if the raw materials for preparing the modified bismaleimide prepolymer also includes other allyl compounds, the modified allyl compound and the other allyl compounds are heated together to the molten state.

An embodiment of the present disclosure further provides use of the modified bismaleimide prepolymer as described above in preparation of resins.

Furthermore, the present disclosure also provides a modified resin composition, wherein the modified resin composition consists of a curing accelerator, an inorganic filler, and the modified bismaleimide prepolymer as described above.

Further, in the raw materials for preparing the modified resin, the modified bismaleimide prepolymer is 50 to 100 parts by mass, a mass fraction of the inorganic filler is 10 to 30 parts by mass, and a mass fraction of the curing accelerator is 1 to 5 parts by mass.

In some of the embodiments, the inorganic filler is silica powder, and the curing accelerator is dicumyl peroxide.

Another embodiment of the present disclosure also provides a thermosetting resin composition. Raw material of the thermosetting resin composition includes the modified bismaleimide prepolymer as described above.

The thermosetting composition has higher glass transition temperature and decomposition temperature, high heat resistance, low water absorption, high modulus, and low dielectric constant and dielectric loss value.

In some of the embodiments, the raw materials of the thermosetting resin composition include by mass:

| | |
|---|---|
| the modified bismaleimide prepolymer | 50 parts to 100 parts; |
| cyanate resin | 30 parts to 80 parts; |
| other functional resin | 5 parts to 30 parts; and |
| inorganic filler | 0 to 30 parts; | wherein the other functional resin is at least one selected from the group consisting of epoxy resin, benzoxazine, polyphenylene ether, and hydrocarbon resin.

In the above thermosetting composition, by adjusting the composition ratio of the modified bismaleimide prepolymer, cyanate resin, other functional resin and other ingredients, the water absorption, dielectric constant and dielectric loss value of the resin are further reduced. At the same time, the modified bismaleimide prepolymer, which has improved resin modulus and heat resistance, can be used to prepare high-performance printed circuit boards with high temperature resistance and aging resistance, integrated circuit packaging, high frequency and high speed, etc., so as to promote the development of high-end integrated circuits.

In some of the embodiments, the raw materials of the thermosetting resin composition include 50 to 80 parts by mass of modified bismaleimide prepolymer.

In some of the embodiments, the raw materials of the thermosetting resin composition include 30 to 60 parts by mass of cyanate resin.

In some of the embodiments, the raw materials of the thermosetting resin composition include 5 to 15 parts by mass of other functional resin.

In some of the embodiments, the raw materials of the thermosetting resin composition include 10 to 30 parts by mass of the inorganic filler.

The raw materials for preparing the thermosetting resin composition include by mass:

| | |
|---|---|
| the modified bismaleimide prepolymer | 50 parts to 80 parts; |
| cyanate resin | 30 parts to 60 parts; |
| other functional resin | 5 parts to 15 parts; and |
| inorganic filler | 10 parts to 30 parts. |

In some of the embodiments, the ester resin as described above is at least one selected from the group consisting of bisphenol A cyanate resin, novolac cyanate resin, bisphenol F cyanate resin, multifunctional cyanate resin, bisphenol M cyanate resin, bisphenol E cyanate resin, and dicyclopentadiene bisphenol cyanate resin.

In some of the embodiments, the above-mentioned inorganic filler is at least one selected from the group consisting of zirconium vanadate, zirconium tungstate, hafnium tungstate, glass ceramics, eucryptite, silicon dioxide, quartz, mica powder, titanium dioxide, magnesium oxide, magnesium hydroxide, talc powder, alumina, silicon carbide, boron nitride, aluminum nitride, molybdenum oxide, barium sulfate, zinc molybdate, zinc borate, zinc stannate, zinc oxide, strontium titanate, barium titanate, calcium titanate, clay, and kaolin.

In some of the embodiments, the raw material of the thermosetting resin composition further comprises an auxiliary agent. The auxiliary agent is at least one selected from the group consisting of a curing accelerator, a coupling agent, and a toughening agent.

The above-mentioned curing accelerator, coupling agent and toughening agent can be selected from curing accelerators, coupling agents and toughening agents commonly used in the art. For example, the curing accelerator can be selected from the group consisting of imidazoles, such as 2-methylimidazole, 2-phenylimidazole, 2-ethyl-4methyl-imidazole, or at least one selected from the group consisting of organic metal salts, such as zinc octoate, zinc isooctanoate, stannous octoate, dibutyltin dilaurate, zinc naphthenate, cobalt naphthenate, aluminum acetylacetonate, cobalt acetylacetonate, and copper acetylacetonate.

An embodiment of the present disclosure also provides use of the thermosetting resin composition as described above and/or the modified resin composition as described above in the preparation of circuit substrates.

The thermosetting composition and/or the modified resin have excellent heat resistance, low water absorption, high modulus, and low dielectric constant and dielectric loss value. Once the thermosetting composition and/or the modified resin is used in the preparation of circuit substrates, the circuit substrate with excellent heat resistance, low water absorption, high modulus, and low dielectric constant and dielectric loss value can be obtained.

The above-mentioned circuit substrates include, but are not limited to, packaging films, substrates, and printed circuit boards.

Furthermore, the present disclosure also provides a composite resin. The composite resin is prepared from raw materials comprising any of the thermosetting resin compositions and/or the modified resin as described above.

The composite resin has excellent heat resistance, low water absorption, high modulus and low dielectric constant and dielectric loss value.

An embodiment of the present disclosure also provides a prepreg. The prepreg comprises a reinforcing material and a resin material supported on the reinforcing material. The resin material is the composite resin as described above.

In some of the embodiments, the reinforcing material is selected from the group consisting of inorganic fiber materials and organic fiber materials.

Inorganic fiber materials comprise, but are not limited to, glass fiber, carbon fiber, silicon carbide fiber and asbestos fiber. Organic fiber materials comprise, but are not limited to, nylon, ultra-high molecular weight polyethylene fibers, aramid fibers, polyimide fibers, polyester fibers, and cotton fibers.

Glass fibers include E, NE, D, S, T and other different types of glass fibers.

Further, the preparation of the prepreg as described above includes following steps S20 to S30.

Step S20: the thermosetting resin composition and/or the modified resin as described above is prepared into a resin glue solution.

In some of the embodiments, step S20 includes following steps S21 and S22.

Step S21: the modified bismaleimide prepolymer, cyanate resin and other functional resins are mixed with an organic solvent to obtain a mixture.

In some of the embodiments, the organic solvent as described above is at least one selected from the group consisting of methyl ethyl ketone, toluene, and propylene glycol methyl ether. Furthermore, the organic solvent is at least one selected from the group consisting of a mixed solvent of methyl ethyl ketone, toluene and propylene glycol methyl ether, wherein a mass ratio of methyl ethyl ketone, toluene and propylene glycol methyl ether is 1:1:1.

Step S22: the mixture, inorganic fillers and other auxiliary agents are mixed to obtain a uniform resin glue solution.

Step S30: the reinforcing material is immersed in the resin glue solution obtained in step S20 and then heated to obtain a prepreg.

In some of the embodiments, in step S30, heating is performed at 130° C. to 250° C. for 2 min to 10 min.

An embodiment of the present disclosure also provides a laminated board. Raw materials for preparing the laminated board comprise the prepreg as described above.

It can be understood that an amount of the prepreg used in raw material for preparing the laminated board can be adjusted according to actual applications.

In one of the embodiments, one or both sides of the above-mentioned laminated board are covered with metal foil. Thus, the laminated board is a laminated board with the metal foil.

It can be understood that the above-mentioned metal foil may be a copper foil or an aluminum foil. Their thickness is not particularly limited, and can be adjusted according to actual applications. Specifically, the above-mentioned metal foil is a copper foil, and the above-mentioned laminated board is a copper-clad board.

In some of the embodiments, the metal foil has a thickness of 3 μm to 70 μm.

Further, the preparation of the laminated board as described above includes following step S40.

Step S40: the above-mentioned prepreg is hot-pressed under vacuum conditions to obtain a laminated board.

In some of the embodiments, the process parameters of hot-pressing are a vacuum degree<2 kPa, a temperature from 150° C. to 300° C., a pressure from 10 kgf/cm2 to 30 kgf/cm2, and time from 200 min to 400 min.

It can be understood that when the raw materials for preparing the laminated board comprises two or more prepregs, the prepregs are laminated and subjected to hot-pressing.

The laminated board as described above has excellent heat resistance, low water absorption, high modulus and low dielectric constant and dielectric loss value, and can be used to prepare high-performance printed circuit boards with high temperature resistance and aging resistance, integrated circuit packaging, high frequency and high speed, etc., so as to promote the development of high-end integrated circuits.

The present disclosure will be described below in conjunction with specific embodiments. However, the present disclosure is not limited to the following embodiments. It should be understood that the appended claims summarize the scope of the present disclosure. Those skilled in the art, under the guidance of the concept of the present disclosure, should realize that certain changes made to the various embodiments of the present disclosure would be covered by the spirit and scope of the claims of the present disclosure.

Synthesis Example 1

1) Under a nitrogen atmosphere, 2 mol of phenol was added into a four-necked flask equipped with a dropping funnel, condenser, stirrer and thermometer, and heated to 100° C. 10 g of catalyst (boron trifluoride ether) was added. Then 1 mol of DCDP was added dropwise with the dropping rate being controlled such that DCDP can be completely added within 5 h. Then the resultant was heat-preserved for 2 h and then cooled to room temperature. Then, phenol and unreacted DCPD were removed by distillation under reduced pressure. After washing with water, solvent butanone was added, followed by filtration and distillation to remove solvent and part of water, then the remainder was poured out and cooled, thus obtaining DCPD phenol resin for use, which is represented by:

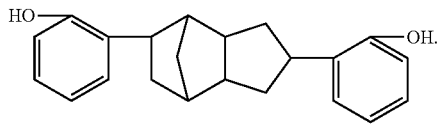 [SMILES: Oc1ccccc1C1CC2C3CC(c4ccccc4O)C(C3)C2C1]

2) Under a nitrogen atmosphere, 1 mol of 4-allyloxybenzoic acid and 1 mol of thionyl chloride were added in a three-necked flask filled with toluene, and were react under reflux at 60° C. for 5 h until the solution became clear. After the reaction, the excess toluene and thionyl chloride were distilled off under reduced pressure, thus obtaining 4-allyloxybenzoyl chloride as a pale yellow liquid for use.

3) 2 mol of 4-allyloxy benzoyl chloride and 1 mol of DCPD phenol resin were diluted with tetrahydrofuran. Then triethylamine was added to the diluent of DCPD phenol resin, while the diluent of 4-allyloxybenzoyl chloride was added dropwise slowly. After refluxing at 60° C. for 24 hours, the suspension was filtered while hot, and the filtrate was retained. After cooling, white crystals were precipitated and recrystallized with tetrahydrofuran, thus obtaining the modified allyl compound A, which is represented by:

(1-3)

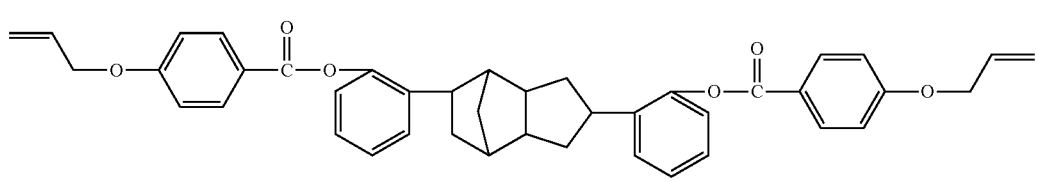

wherein the DCPD is

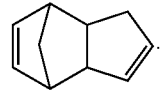

Synthesis Example 2

1) Under a nitrogen atmosphere, 2 mol of phenol was added into a four-necked flask equipped with a dropping funnel, condenser, stirrer and thermometer, and heated to 100° C. 15 g of catalyst (boron trifluoride ether) was added. Then 1 mol of TCDP was added dropwise with the dropping rate being controlled such that the compound TCDP can be completely added within 5 h. Then the resultant was heat-preserved for 2 h and then cooled to room temperature. Then, phenol and unreacted compound TCPD were removed by distillation under reduced pressure. After washing with water, solvent butanone was added, followed by filtration and distillation to remove solvent and part of water, then the remainder was poured out and cooled, thus obtaining a first intermediate for use, which is represented by:

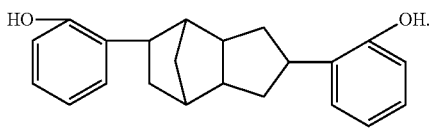 [SMILES: Oc1ccccc1C1CC2C3CC(c4ccccc4O)C(C3)C2C1]

2) Under a nitrogen atmosphere, 1 mol of 4-allyloxybenzoic acid and 1 mol of thionyl chloride were added in a three-necked flask filled with toluene, and were react under reflux at 60'C for 5 h until the solution became clear. After the reaction, the excess toluene and thionyl chloride were distilled off under reduced pressure, thus obtaining 4-allyloxybenzoyl chloride as a pale yellow liquid for use.

3) 2 mol of 4-allyloxy benzoyl chloride and 1 mol of the first intermediate were diluted with tetrahydrofuran. Then triethylamine was added to the diluent of the first intermediate, while the diluent of 4-allyloxybenzoyl chloride was added dropwise slowly. After refluxing at 60° C. for 24 hours, the suspension was filtered while hot, and the filtrate was retained. After cooling, white crystals were precipitated and recrystallized with tetrahydrofuran, thus obtaining the modified allyl compound B, which is re sented by:

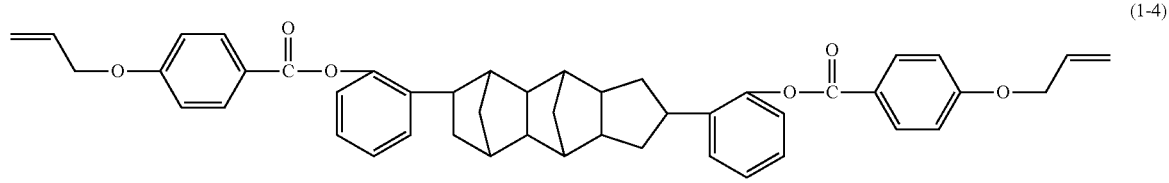 [SMILES: C=CCOc1ccc(C(=O)Oc2ccccc2C2CC3C(C2)C2CC3C3C4CC(c5ccccc5OC(=O)c5ccc(OCC=C)cc5)C(C4)C23)cc1]

(1-4)

wherein the TCPD is

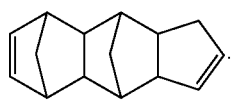 [SMILES: C1=CC2C(C1)C1CC2C2C3C=CC(C3)C12]

3) 2 mol of 4-allyloxy benzoyl chloride and 1 mol of the first intermediate were diluted with tetrahydrofuran. Then triethylamine was added to the diluent of the first intermediate, while the diluent of 4-allyloxybenzoyl chloride was added dropwise slowly. After refluxing at 60° C. for 24 hours, the suspension was filtered while hot, and the filtrate was retained. After cooling, white crystals were precipitated and recrystallized with tetrahydrofuran, thus obtaining the modified allyl compound C, which is represented by:

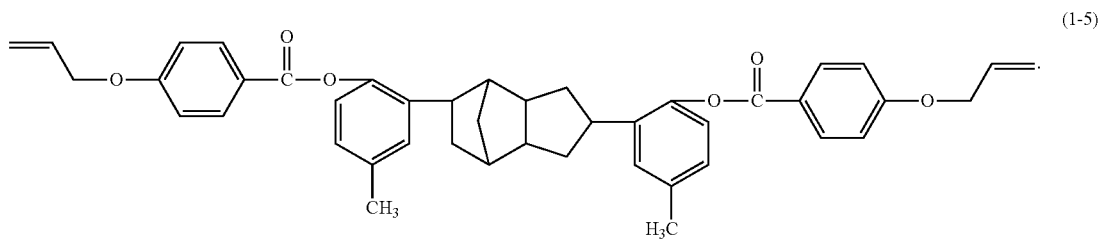 [SMILES: C=CCOc1ccc(C(=O)Oc2ccc(C)cc2C2CC3C4CC(c5cc(C)ccc5OC(=O)c5ccc(OCC=C)cc5)C(C4)C3C2)cc1]

(1-5)

Synthesis Example 3

1) Under a nitrogen atmosphere, 2 mol of p-cresol was added into a four-necked flask equipped with a dropping funnel, condenser, stirrer and thermometer, and heated to 100° C. 15 g of catalyst (boron trifluoride ether) was added. Then 1 mol of DCDP was added dropwise with the dropping rate being controlled such that DCDP can be completely added within 5 h. Then the resultant was heat-preserved for 2 h and then cooled to room temperature. Then, phenol and unreacted compound 2 were removed by distillation under reduced pressure. After washing with water, solvent butanone was added, followed by filtration and distillation to remove solvent and part of water, then the remainder was poured out and cooled, thus obtaining a first intermediate for use, which is represented by:

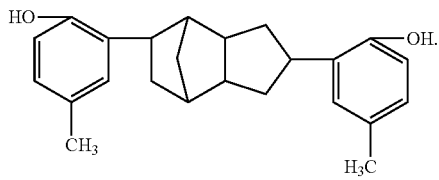

2) Under a nitrogen atmosphere, 1 mol of 4-allyloxybenzoic acid and 1 mol of thionyl chloride were added in a three-necked flask filled with toluene, and were react under reflux at 60° C. for 5 h until the solution became clear. After the reaction, the excess toluene and thionyl chloride were distilled off under reduced pressure, thus obtaining 4-allyloxybenzoyl chloride as a pale yellow liquid for use.

The modified allyl compound A was applied to the examples as below.

Example 1

1) 80 parts of the modified allyl compound A were heated to a molten state, 100 parts of bismaleimide resin were added, and prepolymerization was carried out at 150'C for 60 min followed by cooling, thus obtaining a modified bismaleimide prepolymer A.

2) 50 parts of the above-mentioned modified bismaleimide prepolymer A, 30 parts of bisphenol A cyanate ester resin and 5 parts of DCPD benzoxazine were sequentially diluted in a mixed solvent of butanone, toluene and propylene glycol with a mass ratio of 1:1:1. Under stirring, 10 parts of fused silica and 1 part of 2-methylimidazole were further added with continuing stirring, thus obtaining a uniform glue of the resin composition of the modified bismaleimide prepolymer.

3) #2116 type glass fiber cloth (basis weight 105 g/m² was immersed in the glue of the resin composition of the modified bismaleimide prepolymer, and then baked in a hot air circulating oven at 180° C. for 3 min, obtaining a prepreg with a resin content of 50 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and pressure of 20 kgf/cm², following a procedure of 180° C.*1 h+200° C.*2 h+240° C.*2 h, the laminate was prepared into a copper-clad laminated board with a thickness of 0.6 mm.

Example 2

1) 80 parts of the modified allyl compound A was heated to a molten state, 100 parts of bismaleimide resin was added, and prepolymerization was carried out at 150° C. for 60 min followed by cooling, thus obtaining a modified bismaleimide prepolymer A.

2) 80 parts of the above-mentioned modified bismaleimide prepolymer A, 60 parts of bisphenol A cyanate ester resin and 15 parts of DCPD benzoxazine were diluted in a mixed solvent of butanone, toluene and propylene glycol with a mass ratio of 1:1:1. Under stirring, 30 parts of fused silica and 5 part of 2-methylimidazole were further added with continuing stirring, thus obtaining a uniform a glue of the resin composition of the modified bismaleimide prepolymer.

3) #2116 type glass fiber cloth (basis weight 105 g/m$^2$) was immersed in the glue of the resin composition of the modified bismaleimide prepolymer, and then baked in a hot air circulating oven at 180° C. for 3 min, obtaining a prepreg with a resin content of 55 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm$^2$, following a procedure of 180° C.*1 h+200° C.*2 h+240° C.*2 h, the laminate was prepared into a copper clad laminated board with a thickness of 0.6 mm.

Example 3

1) 80 parts of the modified allyl compound A was heated to a molten state, 100 parts of bismaleimide resin was added, and prepolymerization was carried out at 150° C. for 60 min followed by cooling, thus obtaining a modified bismaleimide prepolymer A.

2) 65 parts of the above-mentioned modified bismaleimide prepolymer A, 45 parts of bisphenol A cyanate ester resin and 10 parts of DCPD benzoxazine were diluted in a mixed solvent of butanone, toluene and propylene glycol with a mass ratio of 1:1:1. Under stirring, 20 parts of fused silica and 3 part of 2-methylimidazole were further added with continuing stirring, thus obtaining a uniform a glue of the resin composition of the modified bismaleimide prepolymer.

3) #2116 type glass fiber cloth (basis weight 105 g/m$^2$) was immersed in the glue of the resin composition of the modified bismaleimide prepolymer, and then baked in a hot air circulating oven at 180° C. for 3 min, obtaining a prepreg with a resin content of 56 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm$^2$, following a procedure of 180° C.*1 h+200° C.*2 h+240° C.*2 h, the laminate was prepared into a copper clad laminated board with a thickness of 0.6 mm.

Example 4

1) 80 parts of the modified allyl compound A was heated to a molten state, 100 parts of bismaleimide resin was added, and prepolymerization was carried out at 150° C. for 60 min followed by cooling, thus obtaining a modified bismaleimide prepolymer A.

2) 90 parts of the above-mentioned modified bismaleimide prepolymer A, 70 parts of bisphenol A cyanate ester resin and 20 parts of DCPD benzoxazine were diluted in a mixed solvent of butanone, toluene and propylene glycol with a mass ratio of 1:1:1. Under stirring, 5 parts of fused silica and 2 part of 2-methylimidazole were further added with continuing stirring, thus obtaining a uniform a glue of the glue of the resin composition of the modified bismaleimide prepolymer.

3) #2116 type glass fiber cloth (basis weight 105 g/m$^2$) was immersed in the glue of the resin composition of the modified bismaleimide prepolymer, and then baked in a hot air circulating oven at 180° C. for 3 min, obtaining a prepreg with a resin content of 49 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm$^2$, following a procedure of 180° C.*1 h+200° C.*2 h+240° C.*2 h. the laminate was prepared into a copper clad laminated board with a thickness of 0.6 mm.

Example 5

1) 40 parts of the modified allyl compound A and 40 parts of allyl bisphenol A were heated to a molten state, 100 parts of bismaleimide resin was added, and prepolymerization was carried out at 150° C. for 60 min followed by cooling, thus obtaining a modified bismaleimide prepolymer B.

2) 50 parts of the above-mentioned modified bismaleimide prepolymer B, 30 parts of bisphenol A cyanate ester resin and 5 parts of DCPD benzoxazine were diluted in a mixed solvent of butanone, toluene and propylene glycol with a mass ratio of 1:1:1. Under stirring, 10 parts of fused silica and 1 part of 2-methylimidazole were further added with continuing stirring, thus obtaining a uniform a glue of the resin composition of the modified bismaleimide prepolymer.

3) #2116 type glass fiber cloth (basis weight 105 g/m$^2$) was immersed in the glue of the resin composition of the modified bismaleimide prepolymer, and then baked in a hot air circulating oven at 180° C. for 3 min, obtaining a prepreg with a resin content of 50 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm$^2$, following a procedure of 180° C.*1 h+200° C.*2 h+240° C.*2 h, the laminate was prepared into a copper clad laminated board with a thickness of 0.6 mm.

Example 6

1) 80 parts of the modified allyl compound A was heated to a molten state, 100 parts of bismaleimide resin was added, and prepolymerization was carried out at 150° C. for 60 min followed by cooling, thus obtaining a modified bismaleimide prepolymer A.

2) 50 parts of the above-mentioned modified bismaleimide prepolymer A, 30 parts of bisphenol A cyanate ester resin and 5 parts of DCPD epoxy resin were diluted in a mixed solvent of butanone, toluene and propylene glycol with a mass ratio of 1:1:1. Under stirring, 10 parts of fused silica and 1 part of 2-methylimidazole were further added with continuing stirring, thus obtaining a uniform a glue of the resin composition of the modified bismaleimide prepolymer.

3) #2116 type glass fiber cloth (basis weight 105 g/m²) was immersed in the glue of the resin composition of the modified bismaleimide prepolymer, and then baked in a hot air circulating oven at 180° C. for 3 min, obtaining a prepreg with a resin content of 50 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm², following a procedure of 180° C.*1 h+200° C.*2 h+240° C.*2 h, the laminate was prepared into a copper clad laminated board with a thickness of 0.6 mm.

Comparative Example 1

1) 80 parts of the modified allyl compound A and 40 parts of allyl bisphenol A were heated to a molten state, 100 parts of bismaleimide resin was added, and prepolymerization was carried out at 150° C. for 60 min followed by cooling, thus obtaining a modified bismaleimide prepolymer C.

2) 50 parts of the above-mentioned modified bismaleimide prepolymer C, 30 parts of bisphenol A cyanate ester resin and 5 parts of DCPD benzoxazine were diluted in a mixed solvent of butanone, toluene and propylene glycol with a mass ratio of 1:1:1. Under stirring, 10 parts of fused silica and 1 part of 2-methylimidazole were further added with continuing stirring, thus obtaining a uniform glue of the resin composition of the modified bismaleimide prepolymer.

3) #2116 type glass fiber cloth (basis weight 105 g/m²) was immersed in the glue of the resin composition of the modified bismaleimide prepolymer, and then baked in a hot air circulating oven at 180° C. for 3 min, obtaining a prepreg with a resin content of 50 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm², following a procedure of 180° C.*1 h+200° C.*2 h+240° C.*2 h, the laminate was prepared into a copper clad laminated board with a thickness of 0.6 mm.

Comparative Example 2

1) 50 parts of the bismaleimide resin, 30 parts of bisphenol A cyanate ester resin and 5 parts of DCPD benzoxazine were diluted in a mixed solvent of butanone, toluene and propylene glycol with a mass ratio of 1:1:1. Under stirring, 10 parts of fused silica and 1 part of 2-methylimidazole were further added with continuing stirring, thus obtaining a uniform glue of the composition of the bismaleimide resin.

3) #2116 type glass fiber cloth (basis weight 105 g/m²) was immersed in the glue of the composition of the bismaleimide resin, and then baked in a hot air circulating oven at 180° C. for 3 min, obtaining a prepreg with a resin content of 50 wt %.

4) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm², following a procedure of 180° C.*1 h+200° C.*2 h+240° C.*2 h+260° C.*2 h, the laminate was prepared into a copper clad laminated board with a thickness of 0.6 mm.

Comparative Example 3

Comparative Example 3 was substantially the same as Example 1, except that the modified allyl compound used in Comparative Example 3 had a structural formula represented by:

It was prepared in a substantially same method as that for preparing the modified allyl compound as above, except that phenol is replaced with hydroquinone in step 1).

1) 80 parts of the modified allyl compound D was heated to a molten state, 100 parts of bismaleimide resin was added, and prepolymerization was carried out at 150° C. for 60 m followed by cooling, thus obtaining a modified bismaleimide prepolymer D. Other raw materials and preparation process conditions were the same as in Example 1.

The raw materials for Examples 1 to 6 and Comparative Examples 1 to 3 are shown in Table 1.

TABLE 1

| Component | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|
| bismaleimide prepolymer A | 50 | 80 | 65 | 90 | 0 | 50 | 0 | 0 | 0 |
| bismaleimide prepolymer B | 0 | 0 | 0 | 0 | 50 | 0 | 0 | 0 | 0 |
| bismaleimide prepolymer C | 0 | 0 | 0 | 0 | 0 | 0 | 50 | 0 | 0 |
| bismaleimide prepolymer D | 0 | 0 | 0 | 0 | 0 | 0 | 0 | 0 | 50 |
| bismaleimide resin | 0 | 0 | 0 | 0 | 0 | 0 | 0 | 50 | 0 |
| bisphenol A cyanate | 30 | 60 | 45 | 70 | 30 | 30 | 30 | 30 | 30 |
| DCPD benzoxazine | 5 | 15 | 10 | 20 | 5 | 0 | 0 | 0 | 5 |
| DCPD epoxy resin | 0 | 0 | 0 | 0 | 0 | 5 | 5 | 5 | 0 |
| fused silica | 10 | 30 | 20 | 5 | 10 | 10 | 10 | 10 | 10 |
| 2-methylimidazole | 1 | 5 | 3 | 2 | 1 | 1 | 1 | 1 | 1 |

Performance Testing

Performance tests were performed on the copper-clad laminated board produced in Examples 1 to 6 and Comparative Examples 1 to 3.

TABLE 2

| Test items | Resin compatibility | Peel strength (lb/in) | Tg (° C.) | Td (° C.) | Elastic modulus (Gpa) | Dk/Df | Water absorption (%) |
|---|---|---|---|---|---|---|---|
| Example 1 | OK | 6.8 | 285 | 390 | 32/30 | 3.37/0.004 | 0.08 |
| Example 2 | OK | 6.6 | 290 | 400 | 31/29 | 3.35/0.003 | 0.10 |
| Example 3 | OK | 6.7 | 280 | 385 | 32/30 | 3.30/0.003 | 0.09 |
| Example 4 | OK | 6.3 | 270 | 380 | 29/27 | 3.46/0.005 | 0.15 |
| Example 5 | OK | 6.3 | 265 | 370 | 28/26 | 3.50/0.006 | 0.15 |
| Example 6 | OK | 6.9 | 265 | 380 | 28/26 | 3.60/0.007 | 0.12 |
| Comparative Example 1 | OK | 6.3 | 270 | 370 | 27/25 | 3.92/0.008 | 0.18 |
| Comparative Example 2 | Slight precipitation | 6.0 | 260 | 360 | 26/24 | 4.01/0.009 | 0.20 |
| Comparative Example 3 | OK | 6.0 | 265 | 364 | 28/26 | 3.82/0.010 | 0.22 |

Example 7

1) 70 parts of the modified allyl compound A was heated to a molten state, 100 parts of bismaleimide resin was added, and prepolymerization was carried out at 150° C. for 60 min followed by cooling, thus obtaining a modified bismaleimide prepolymer A. Then the modified bismaleimide prepolymer was dissolved in a mixed solvent of butanone, toluene and propylene glycol with a mass ratio of 1:1:1. Under stirring, with 100 parts of modified bismaleimide prepolymer as a reference, 5 parts of dicumyl peroxide DCP and 30 parts of fused silica were further added with continuing stirring, thus obtaining a uniform glue of the resin composition of the modified bismaleimide prepolymer.

2) #2116 type glass fiber cloth (basis weight 105 g/m$^2$) was immersed in the glue of the resin composition of the modified bismaleimide prepolymer, and then baked in a hot air circulating oven at 180° C. for 3 min. obtaining a prepreg with a resin content of 50 wt %.

3) 6 sheets of prepregs were laminated, and then the laminate was covered with electrolytic copper foils with a thickness of 12 μm on each of the upper and lower sides. The laminate covered with copper foils was placed in a vacuum press with programmably controlled temperature and pressure. Under vacuum and a pressure of 20 kgf/cm$^2$, following a procedure of 180° C.*1 h+200° C.*2 h+240° C.*2 h, the laminate was prepared into a copper-clad laminated board with a thickness of 0.6 mm.

Example 8

Example 8 was substantially the same as Example 7, except that the modified allyl compound A was replaced with the modified allyl compound B in step 1) of Example 8.

Other steps and conditions were the same as in Example 7.

Example 9

Example 9 was substantially the same as Example 7, except that 70 parts of the modified allyl compound A was replaced with 50 parts of the modified allyl compound A in step 1) of Example 8.

Other steps and conditions were the same as in Example 7.

Example 10

Example 10 was substantially the same as Example 7, except that 70 parts of the modified allyl compound A was replaced with 60 parts of the modified allyl compound A in step 1) of Example 8.

Other steps and conditions were the same as in Example 7.

Comparative Example 4

Comparative Example 4 was substantially the same as Example 7, except that the modified allyl compound A was replaced with 2,2-diallyl bisphenol A (DABPA).

Other steps and conditions were the same as in Example 7.

Comparative Example 5

Comparative Example 5 was substantially the same as Example 7, except that the modified allyl compound A was not added. Other steps and conditions were the same as in Example 7.

The raw materials for Examples 7 to 10 and Comparative Examples 4 to 5 are shown in Table 3.

TABLE 3

| Component | Example 7 | Example 8 | Example 9 | Example 10 | Comparative Example 4 | Comparative Example 5 |
|---|---|---|---|---|---|---|
| Allyl compound A | 70 | 0 | 50 | 0 | 0 | 0 |
| Allyl compound B | 0 | 70 | 0 | 60 | 0 | 0 |
| DABPA | 0 | 0 | 0 | 0 | 70 | 0 |
| Bismaleimide resin | 100 | 100 | 100 | 100 | 100 | 100 |
| Fused silica | 30 | 30 | 30 | 30 | 30 | 30 |
| DCP | 5 | 5 | 5 | 5 | 5 | 5 |

Performance Testing

Performance tests were performed on the copper-clad laminated board produced in Examples 7 to 10 and Comparative Examples 4 to 5:

TABLE 4

| Test items | Resin compatibility | Peel strength (lb/m) | Tg (° C.) | Td (° C.) | Elastic modulus (Gpa) | Dk/Df | Water absorption (%) |
|---|---|---|---|---|---|---|---|
| Example 7 | OK | 7.0 | 340 | 410 | 34/32 | 3.34/0.003 | 0.08 |
| Example 8 | OK | 7.1 | 342 | 411 | 33/31 | 3.31/0.004 | 0.09 |
| Example 9 | OK | 6.9 | 335 | 408 | 32/30 | 3.45/0.004 | 0.10 |
| Example 10 | OK | 6.8 | 330 | 405 | 33/30 | 3.44/0.004 | 0.10 |
| Comparative Example 4 | OK | 6.2 | 320 | 390 | 29/27 | 3.85/0.009 | 0.18 |
| Comparative Example 5 | Slight precipitation | 6.0 | 290 | 380 | 27/25 | 4.10/0.012 | 0.25 |

The above raw materials can be commercially available products as follows:
  Bismaleimide resin (Cat. No. BMI-01), purchased from Honghu Bismaleimide Resin Factory;
  Bisphenol A cyanate (Cat. No. C01MO), purchased from Techia Material;
  Diallyl bisphenol A, purchased from Honghu Bismaleimide Resin Factory;
  DCPD benzoxazine (Cat. No. LPY 11051), purchased from Huntsman;
  DCPD epoxy resin (Cat. No. XD-1000), purchased from Nippon Kayaku;
  Fused silica (Cat. No. MEGASIL 525), purchased from Sibelco;
  2-Methylimidazole, purchased from Shikoku Chemicals;
  DCP, purchased from Hongbaoli Chemical.

The test methods are as follows:
1) Peel strength: the test method is under IPC-TM-650 2.4.8;
2) Glass transition temperature (Tg): the test method is under IPC-TM650 2.4.25D;
3) Thermal decomposition temperature (Td): the test method is under IPC-TM650 2.4.24.6;
4) Elastic modulus: the test method is under GB/T 22315-2008;
5) Water absorption: the test method is under IPC-TM650 2.6.2.1:
6) Dk/Df: the test method is under IPC-TM650 2.5.5.2;
7) Resin compatibility: the resin glue solution is placed in a room-temperature environment and stood to observe whether there is any substance precipitated.

The technical features of the embodiments described above may be arbitrarily combined. For the sake of brevity of description, not all possible combinations of the technical features in the aforementioned embodiments are described. However, as long as there is no contradiction between the combinations of these technical features, all should be considered as the scope of this specification.

The above embodiments only represent several examples of the present disclosure, and the description thereof is more specific and detailed, but it should not be construed as restricting the scope of the present disclosure. It should be understood that the applications of the present disclosure are not limited to the above-described examples, and those skilled in the art can make modifications and changes in accordance with the above description, all of which are within the protection scope of the present disclosure. Therefore, the protection scope of the present disclosure shall be defined by the appended claims.

What is claimed is:
1. A modified allyl compound represented by formula (1):

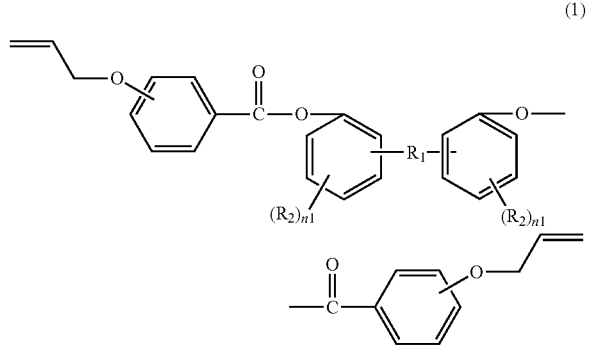

wherein R₁ is represented by formula (2):

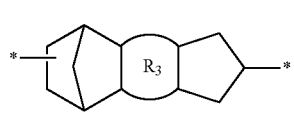
(2)

R₃ is absent or is selected from a bicycloheptyl group and a group obtained by condensation of two or more bicycloheptyl groups: * indicates an attachment site;

R₂ at each occurrence is independently selected from H and a linear alkyl group having 1 to 10 carbon atoms; n1 at each occurrence is independently selected from any integer from 1 to 4.

2. The modified allyl compound according to claim 1, wherein R₁ is selected from any one of formula (2-a) and formula (2-b):

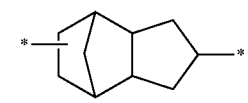
(2-a)

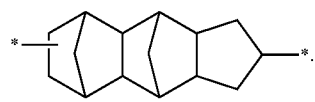
(2-b)

3. The modified allyl compound according to claim 1, represented by formula (1-1);

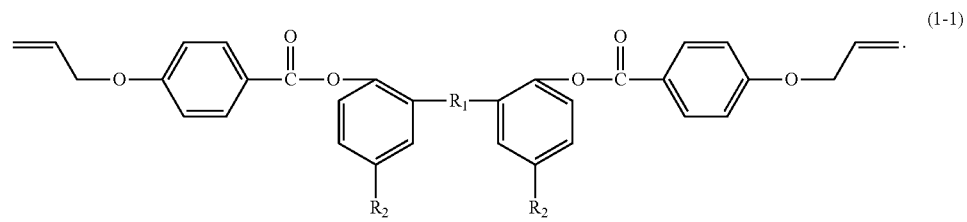
(1-1)

4. The modified allyl compound according to claim 3, wherein R₂ is H.

5. The modified allyl compound according to claim 1, represented by formula (1-3):

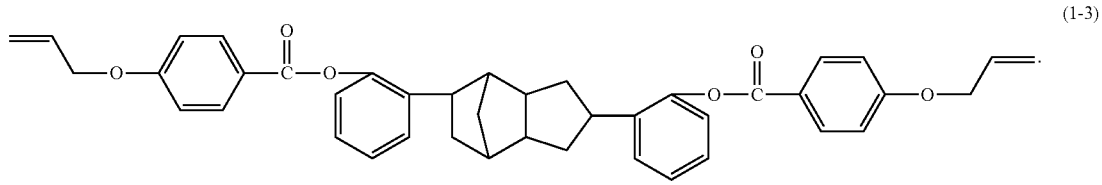 [SMILES: C=CCOc1ccc(C(=O)Oc2ccccc2C2CC3C4CC(c5ccccc5OC(=O)c5ccc(OCC=C)cc5)C(C4)C3C2)cc1]
(1-3)

6. The modified allyl compound according to claim 1, represented by formula (1-4):

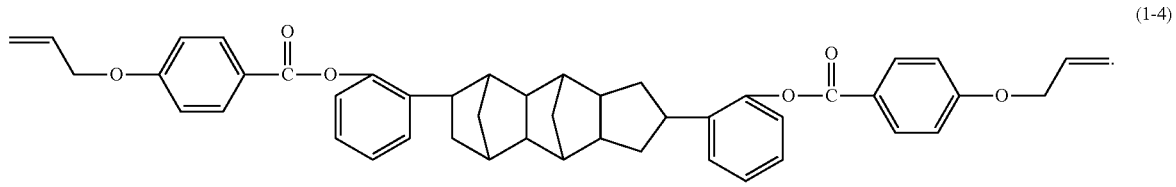 [SMILES: C=CCOc1ccc(C(=O)Oc2ccccc2C2CC3C(C2)C2CC3C3C4CC(c5ccccc5OC(=O)c5ccc(OCC=C)cc5)C(C4)C23)cc1]
(1-4)

7. A modified bismaleimide prepolymer, wherein raw materials for preparing the modified bismaleimide prepolymer comprise bismaleimide resin and the modified allyl compound according to claim 1.

8. The modified bismaleimide prepolymer according to claim 7, wherein the raw materials comprise by mass:

| | |
|---|---|
| the bismaleimide resin | 100 parts; and |
| the modified allyl compound | 40 parts to 100 parts. |

9. The modified bismaleimide prepolymer according to claim 6, wherein the raw materials further comprise other allyl compound being at least one selected from the group consisting of diallyl bisphenol A, diallyl bisphenol S, diallyl bisphenol F, and bisphenol A diallyl ether; wherein a mass ratio of the other allyl compound and the modified propyl compound is (5 to 40): (40 to 80).

10. A modified resin composition, consisting of a curing accelerator, an inorganic filler, and the modified bismaleimide prepolymer according to claim 7.

* * * * *